US007156094B2

(12) United States Patent
Chornyj

(10) Patent No.: US 7,156,094 B2
(45) Date of Patent: Jan. 2, 2007

(54) BREATHING APPARATUS AND PRESSURE VESSELS THEREFOR

(75) Inventor: Nicholas Anthony Chornyj, Fort McMurray (CA)

(73) Assignee: Failsafe Air Vest Corporation, Reno, NV (US)

( * ) Notice: Subject to any disclaimer, the term of this patent is extended or adjusted under 35 U.S.C. 154(b) by 747 days.

(21) Appl. No.: 10/117,325

(22) Filed: Apr. 8, 2002

(65) Prior Publication Data

US 2002/0153009 A1 Oct. 24, 2002

(30) Foreign Application Priority Data

Apr. 6, 2001 (CA) .................................... 2353454
Jul. 19, 2001 (CA) .................................... 2353298

(51) Int. Cl.
*A61M 15/00* (2006.01)

(52) U.S. Cl. ........................... 128/202.19; 128/204.26; 128/205.22

(58) Field of Classification Search ........... 128/201.29, 128/202.19, 204.26, 205.22; 220/585, 586, 220/588, 589, 592, 645, 646, 647, 648
See application file for complete search history.

(56) References Cited

U.S. PATENT DOCUMENTS 1,288,857 A * 12/1918 Farr ...................... 128/205.22
1,419,395 A * 6/1922 Mackenzie .................... 52/511
1,608,264 A * 11/1926 Germano ............... 128/201.22
1,630,209 A * 5/1927 Olgard .................. 128/206.26
1,982,852 A * 12/1934 Bergstrom et al. ............ 285/55
2,109,529 A * 3/1938 Goddard ................. 244/117 R
2,335,038 A * 11/1943 Bridges ....................... 220/646
2,339,554 A * 1/1944 Kuhn ......................... 220/592
2,376,831 A * 5/1945 Stearns ........................ 220/586
2,380,372 A * 7/1945 Alderfer ....................... 244/148
2,381,396 A * 8/1945 Kuhn .......................... 220/592
2,507,778 A * 5/1950 Frey ........................... 220/585
2,844,145 A * 7/1958 Berge .................... 128/205.22
2,844,939 A * 7/1958 Schultz ........................ 60/257
3,074,584 A * 1/1963 Curzon ....................... 220/591
3,228,549 A * 1/1966 Courtney .................... 220/589
3,490,638 A * 1/1970 Francois et al. ............ 220/565
3,540,615 A * 11/1970 Burkley et al. ........ 220/560.13
4,118,262 A * 10/1978 Abbott ....................... 156/175
4,932,403 A * 6/1990 Scholley ................ 128/205.22
4,964,405 A * 10/1990 Arnoth .................. 128/205.17
5,036,845 A * 8/1991 Scholley ................ 128/205.22
5,127,399 A * 7/1992 Scholley ................ 128/205.22
5,188,267 A 2/1993 Sargent et al.
5,287,987 A 2/1994 Gaiser
5,309,571 A 5/1994 Huang
5,370,113 A * 12/1994 Parsons ................. 128/205.22
5,385,262 A * 1/1995 Coquet et al. .............. 220/589

(Continued)

FOREIGN PATENT DOCUMENTS

EP 506256 9/1992

(Continued)

*Primary Examiner*—Aaron J. Lewis
(74) *Attorney, Agent, or Firm*—Dennison, Schultz & MacDonald

(57) ABSTRACT

There is described a wearable garment capable of supplying air to a user comprising a plurality of compartments disposed about the garment, a plurality of air storage vessels for fitting into respective ones of the compartments, an air regulator, a connector for connecting the plurality of air storage vessels to the regulator, and a breathing member connected to the regulator in fluid communication therewith, wherein the breathing member allows a user to receive air from the plurality of air storage vessels.

8 Claims, 10 Drawing Sheets

U.S. PATENT DOCUMENTS

| | | | | |
|---|---|---|---|---|
| 5,522,340 | A * | 6/1996 | Skogman | 114/357 |
| 5,822,838 | A * | 10/1998 | Seal et al. | 29/469.5 |
| 6,357,439 | B1 * | 3/2002 | Cook et al. | 128/205.22 |
| 6,412,484 | B1 * | 7/2002 | Izuchukwu et al. | 128/205.22 |
| 6,412,801 | B1 * | 7/2002 | Izuchukwu et al. | 280/250.1 |
| 6,502,571 | B1 * | 1/2003 | Izuchukwu et al. | 128/202.19 |
| 6,510,849 | B1 * | 1/2003 | Izuchukwu et al. | 128/202.19 |
| 6,510,850 | B1 * | 1/2003 | Izuchukwu et al. | 128/202.19 |
| 6,513,522 | B1 * | 2/2003 | Izuchukwu et al. | 128/202.19 |
| 6,513,523 | B1 * | 2/2003 | Izuchukwu et al. | 128/202.19 |
| 6,526,968 | B1 * | 3/2003 | Izuchukwu et al. | 128/202.19 |
| 6,893,604 | B1 * | 5/2005 | Hauber | 264/516 |

FOREIGN PATENT DOCUMENTS

| | | |
|---|---|---|
| WO | 0076589 | 12/2000 |

* cited by examiner

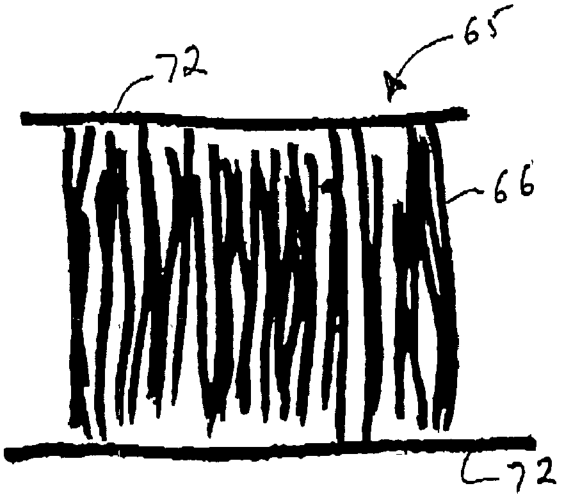
FIGURE 14
FIGURE 15
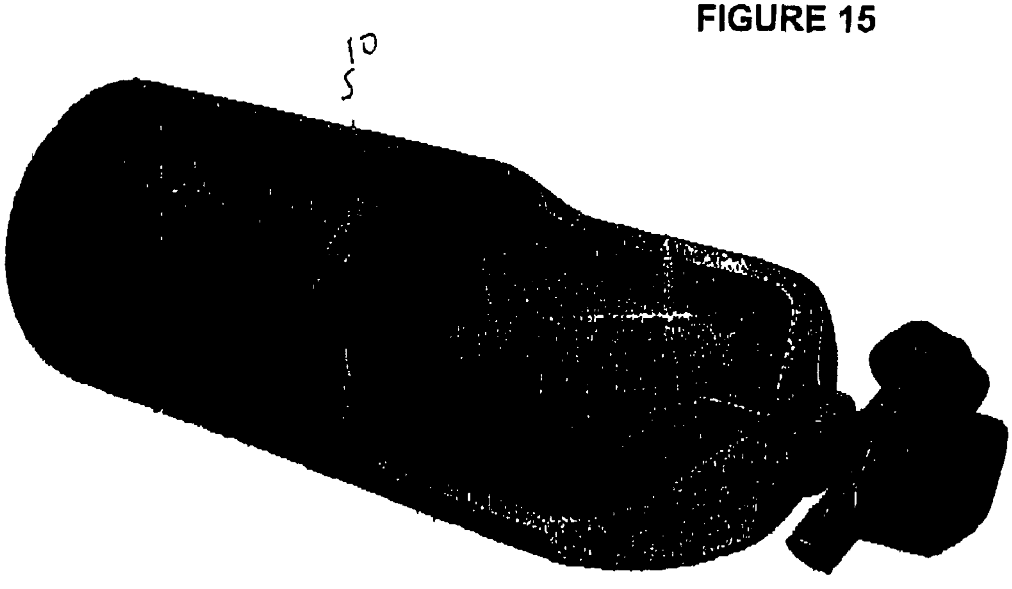
PRIOR ART

BREATHING APPARATUS AND PRESSURE VESSELS THEREFOR

FIELD OF THE INVENTION

The present invention relates to self-contained breathing apparatus, and more particularly to breathing apparatus in the nature of a vest worn by a user having pressurized cylinders or flasks of breathable air distributed in the vest, self-contained underwater breathing apparatus and specifically, self-contained breathing apparatus that may be worn by the user. The apparatus is used for, among other things, firefighting, emergency air supply for workers in hazardous environments or underwater use.

BACKGROUND OF THE INVENTION

The disadvantages of previous air breathing apparatus include their weight, bulk, awkwardness, restrictions they create in closed confinement spaces, their risk of explosion and the marginal minutes of breathable air they provide in both emergency and continuous duty situations.

Previous designs have often put the air supply either high on the back of the user or to the side of the user, causing the user's centre of gravity to be shifted, thus creating strain on the user when wearing the apparatus and making continuous use of the apparatus difficult.

Further, in industry, emergency escape apparatus typically only provide 5 minutes to 15 minutes of breathable air. This gives the user a false sense of security since documented evidence shows that in many cases more time is required. For miners, accidents can require that the miner have one to two hours of breathable air to allow for safe evacuation. Construction workers building additions beside operating gas plants and refineries have found insufficient evacuation routes in the past and found a 5–15 minute emergency air supply was not enough.

Other problems with self-contained breathing apparatus include the fact that they do not compensate for the size of the user, it is a well known fact that a large person consumers more air per minute than a smaller person. Thus by providing the same emergency device to both individuals, the large person will have less time to safely escape the hazardous situation.

One of the main drawbacks to increasing air supply is the weight of tanks to carry the air. These tanks are generally large metal cylinders that are charged to approximately 3000 psi.

One solution to the weight problem is to create composite vessels with a metal liner and a composite structural component. These vessels still however have to be sufficiently strong to prevent failure, and thus the pressure in these vessels is limited.

Another problem with current air vessels, especially filament-epoxy wound containers, is that they have several deficiencies. These vessels do not have a good impact resistence capability, and are susceptible to rupturing if damaged. Further, rupturing of these vessels generally causes fragments to be propelled at high speeds, endangering those near the vessel.

Another problem with fibre-epoxy windings is that they do not withstand adverse environmental conditions very well. Exposure to caustic environments is possible, for example, in firefighting applications or in breathing devices designed for evacuation from chemical or industrial plants. These devices therefore need protection from the adverse environment.

SUMMARY OF THE INVENTION

The present air vest apparatus addresses all of the above problems for existing self-contained breathing apparatus. This vest device is engineered to provide a self-contained breathing apparatus option suited for closed confinement applications in all of the categories for fire fighting, industrial, marine and aircraft environments.

The compactness of the vest, the longer duration of its air supply due to the variety of the number of possible cylinder or flask combinations, its diminished explosive risk and the unique compartmentalization of the vests allows an increased amount of breathable minutes of air in the garments. The air vest incorporates the function of being able to calibrate the breathable minutes of air on an individual basis.

The advantages of the air vest garment can create new categories of field applications as an emergency escape apparatus and as a working ("prolonged use" or "continuous/duty") apparatus. It is envisioned that some of these new categories will include Emergency Preparedness for diplomat personnel, government employees, highrise office workers, police tactical units, armed forces, naval ship personnel, passenger and cargo ship personnel, aircraft personnel, hotel and motel employees, rail workers, drivers transporting hazardous goods, asthmatics requiring a portable oxygen supply, residents living in the proximity of possible hazardous incidents, lab technicians, and construction workers, particularly those working in or near potential hazards.

The air vest technology provides a unique, versatile compact design with considerable flexibility as to the numerous cylinder or flask combinations. Specific job task assignments will dictate: (1) the number of cylinders or flasks; (2) whether the cylinders or flasks are composite or metallic compounds; (3) the size of the cylinders or flasks; and (4) the working pressure of each particular model.

Inasmuch as a preferred objective is to engineer an air vest with minimal thickness, dimensional reductions of the cylinders or flasks will provide reduced vest thickness.

With a view towards allowable working pressures above the "industry-norm", there is provided a high strength flexible over-wrap for use on pressure vessels. Specifically, one aspect of the present invention provides for the use of a carbon composite filament saturated with a liquid rubber compound which is wound around an existing pressure vessel and cured. In a preferred embodiment the carbon composite is Kevlar™.

The carbon fibre over-wrap of the present invention is used to add strength, impact resistance, explosion containment, and exposure protection to any existing pressure vessel.

By alleviating the explosive risk of high pressure cylinders with the incorporation of the containment overwrap, it may become possible to initiate applications to increase the standard working pressures of SCBA (self contained breathing apparatus) and SCUBAs (self contained underwater breathing apparatus).

The containment overwrap should also allow the exterior surface of the composite cylinders or flasks to maintain a pristine quality for an extended number of years relative to prior art in the field.

In order to allow higher air pressure to be used in cylinders, there may additionally be provided a metal braid containment overwrap. The braided containment overwrap creates a net around the cylinder or flask and confines propelled fragments from a ruptured cylinder or flask.

To provide for a user's safety, there are also provided deflector plates which are secured between the cylinders or flasks and the user. These plates are comprised of a new carbon fiber core material, The high pressure cylinders or flasks are attached within pockets of the present vest garment device. The flasks or cylinders are interconnected with low pressure pneumatic hose between each other and the second stage regulator at chest height which supplies air on demand to the respirator-face piece. This design therefore is relatively compact, lightweight and easy to use. A combination high-pressure shut-off valve, first stage regulator and low pressure valve are contained in the regulator-valve body attached to each cylinder or flask. This device regulates the cylinder or flask's working pressure down to 30 psi–60 psi. The reduced pressure is supplied into a low pressure pneumatic hose which interconnects all of the cylinders or flasks to the second stage regulator at chest height on the front of the vest garment.

A further pneumatic hose connects the second-stage regulator and the face-piece. Air pressure is reduced to atmospheric pressure by the second-stage regulator.

In some applications, the pneumatic hose will be replaced with a metal air manifold.

The present invention therefore provides a wearable garment apparatus capable of supplying air to a user comprising a plurality of compartments disposed about said garment; a plurality of air storage means for fitting into respective ones of said compartments; regulator means; conduit for connecting said plurality of air storage means to said regulator means; and a breathing member connected in fluid communication to said regulator means; wherein said breathing means allows a user to receive air from said plurality of air storage means.

The present invention further provides a composite carbon fibre core comprising a first carbon fibre fabric layer; a second carbon fibre fabric layer; and an inner layer of carbon fibre disposed between said first and second layers; wherein said inner layer of carbon fibre has carbon fibres disposed substantially perpendicularly to carbon fibres within said first and second carbon fibre fabric layers.

The present invention still further provides a method for making a composite carbon fibre core comprising the steps of placing a first carbon fibre fabric layer substantially horizontally; creating a second layer through the steps of placing mixed carbon fibre and epoxy materials into a mould; and cutting layers from said mixed materials; placing said second layer over said first layer; placing a third layer of carbon fibre fabric over said second layer; and curing the combination.

The present invention yet further provides an air containment vessel comprising an inner bladder made of rubber; a structural core; an outer rubber cover; and an air outlet; whereby said inner bladder fits concentrically within said core and said core fits concentrically within said outer cover, and whereby said air outlet provides fluid communication for air leaving and entering said vessel.

The present invention still further provides a method of making a composite carbon fibre air containment vessel having an internal bladder, comprising the steps of creating a wax module in the shape of the inside of the air containment vessel; inserting an air inlet tube into one end of said wax module; dipping said wax module into a liquid to form a layer of bladder material on said wax module: allowing said layer to cure; filament winding a carbon fibre core over said bladder layer; curing the carbon fibre core by heating, thereby also melting the wax module; dipping said carbon fibre core into liquid rubber creating an outer rubber layer; and allowing said outer rubber layer to cure.

The present invention still further provides a containment means for a pressurized fluid vessel comprising a plurality of wires wrapped about said vessel; a plurality of fastening means for securing the ends of respective ones of said wires together, said fastening means having energy absorbing means therein to allow controlled expansion of said wire in the event of vessel failure; and whereby each wire can be affixed at a second end to a lug using cones and stoppers within the lug The present invention yet further provides a protective over-wrap for a pressure vessel comprising a carbon composite thread; and a liquid rubber; wherein said carbon composite thread is immersed in said liquid rubber and subsequently wound about said pressure vessel, and wherein said pressure vessel with said carbon composite thread and liquid rubber winding are then cured, The present invention further provides a method of creating a protective over-wrap for pressure vessels comprising the steps of saturating a carbon-composite thread in a liquid rubber compound; winding said saturated thread about said pressure vessel; and curing said pressure vessel and saturated thread; whereby said rubber and carbon composite thread comprise said protective over-wrap.

BRIEF DESCRIPTION OF THE DRAWINGS

Preferred embodiments of the present invention will now be described in greater detail and will be better understood when read in conjunction with the following drawings in which.

DETAILED DESCRIPTION OF THE DRAWINGS

The present invention consists of a compact, lightweight, self contained air breathing apparatus in the form of multiple, high pressure vessels or vessels that are contained within a body vest and in a preferred embodiment are designed to provide a user with at least 30 minutes of breathable air.

Figure 1:
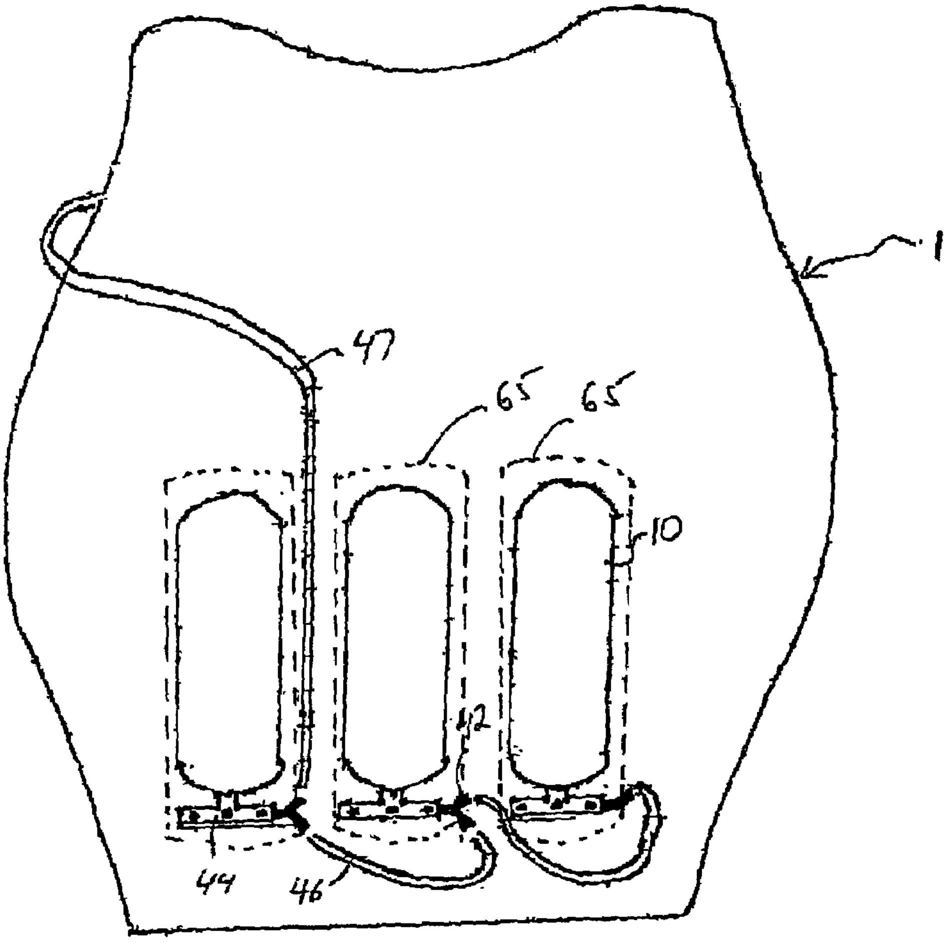
FIG. 1 is a schematical view of the vest apparatus as seen from the rear.
Figure 2:
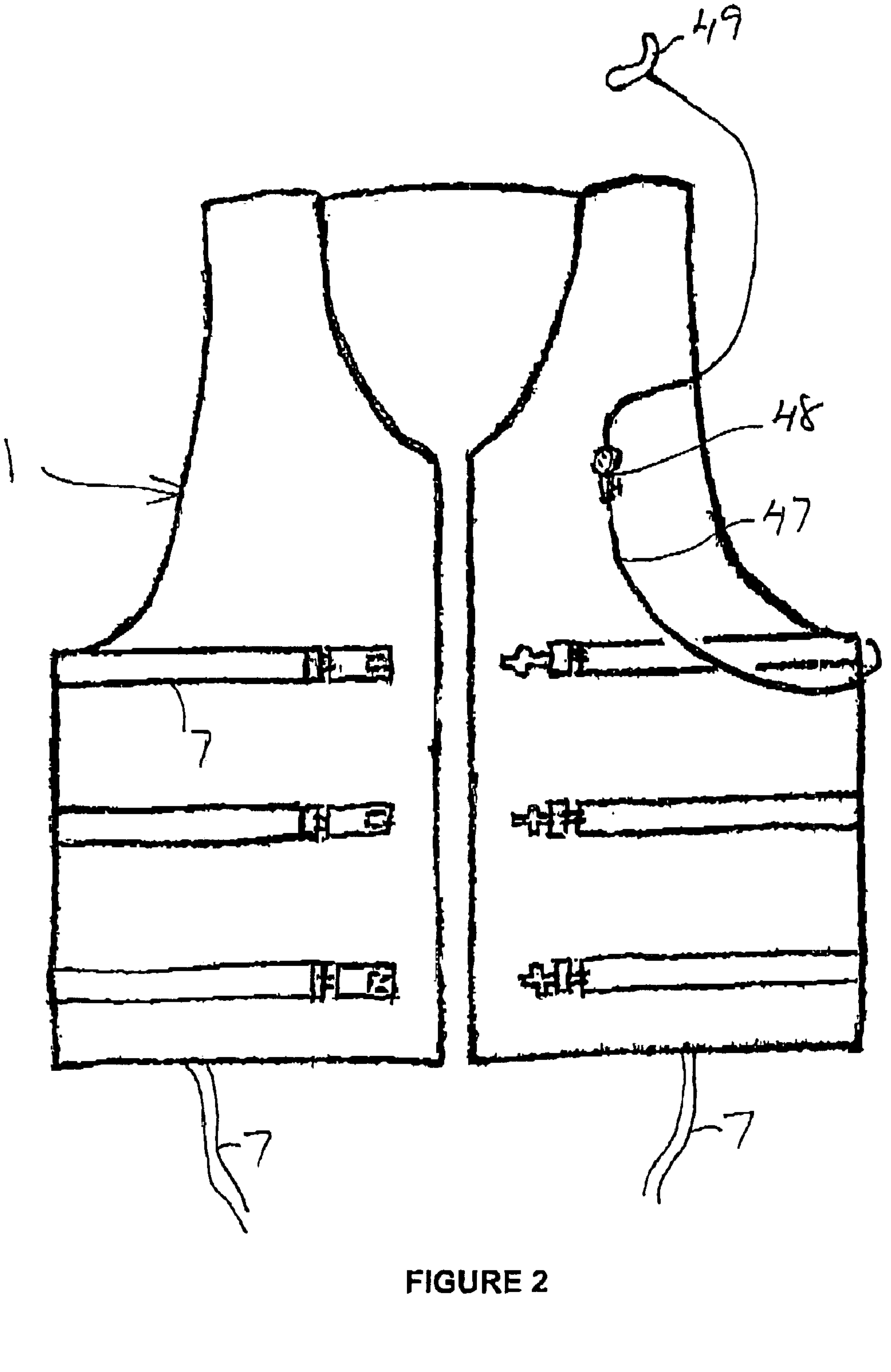
FIG. 2 is a schematical view of the vest apparatus as seen from the front.

Referring to FIGS. 1 and 2, the construction of the vest apparatus 1 in the present invention consists of a series of distinct components that are interconnected in order to provide the functionality of the apparatus. These components include a series of high pressure vessels 10 or vessels that are interconnected, a containment bag 50 (FIG. 11) or device to protect a user in the case of a rupture of one of the high pressure vessels, an explosion shield 65 placed within the vest and between a user and the high pressure vessels in order to further protect a user in the case of an explosion or rupture of one of the vessels, a breathing piece 49, and the vest structure 1 comprised of a material suited to the envisioned use of that particular vest apparatus. Further features such as pressure monitoring sensors and alarms, straps 7 for securing the vest apparatus more securely to a user, regulators, T fittings, etc., may also be included in the vest. Each of these components and how they interconnect will be described in more detail below, starting with preferred air vessels used, including containment means for these vessels to allow them to be charged to a higher pressure, and then deflector means placed within the vest between the vessel and the user, and then the regulators, hoses, and respirators used.

The vest 1 uses a series of interconnected high pressure vessels 1 0. These vessels are illustrated in FIGS. 3 to 6, and in a preferred embodiment are comprised of an entirely non-metal structure to reduce their weight. Vessels 10 are discussed in greater detail below, Other metal embodiments of the vessels could also be used in the present invention, and this disclosure is not intended to limit the type of vessel that may be used within the present vest apparatus. One such vessel that is contemplated is illustrated in Figure and is made by Luxfer USA Limited.

Pressure vessels 10 are preferably chargeable to extremely high working pressures, generally within the range of 4500–7500 PSI. For safety, vessels 10 can be tested up to 15000 PSI. This is compared to the prior art air vessels which are more typically charged in the 3000–4500 PSI range.

Figure 5:
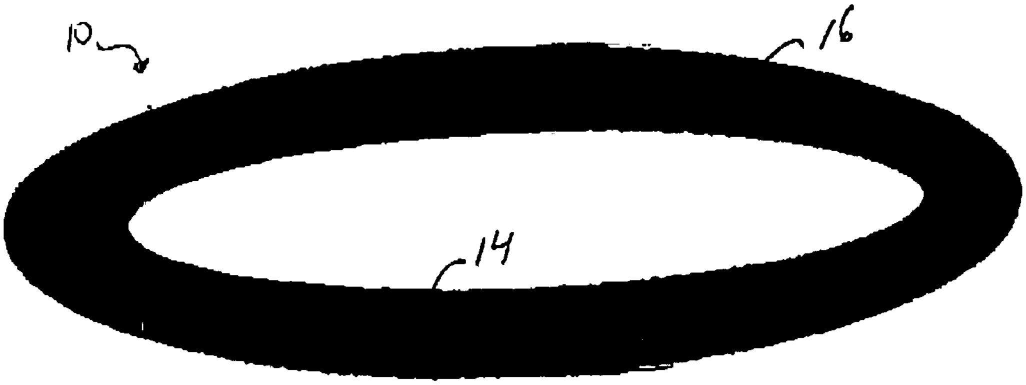
FIG. 5 is a transverse cross-sectional view of an embodiment of the high pressure vessel and fitting shown in FIG. 3.
Figure 9:
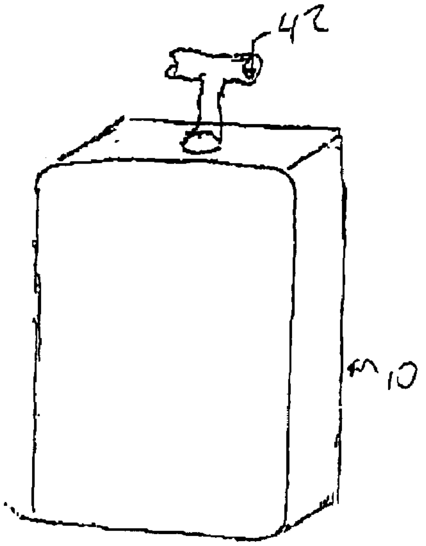
FIG. 9 is a perspective view of a modified shape of an air vessel including a "T" fitting.
Figure 10:
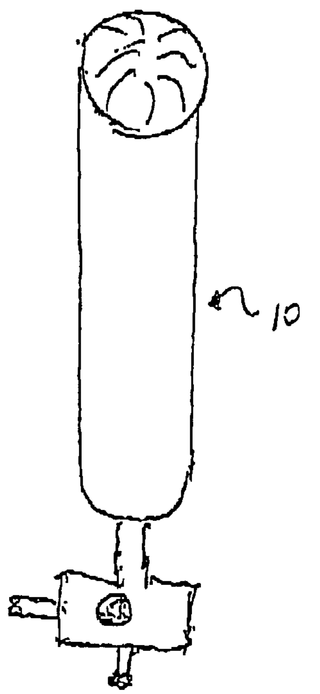
FIG. 10 is a perspective view of another embodiment of a pressure vessel, including a regulator.

Vessels 10 are preferably made of a carbon fibre epoxy and comprise body portion 12 which has a rubber or nylon coating 14 on its inner surface and a rubber or nylon coating 16 on its outer surface. Carbon fibre and epoxy were chosen due to strength and weight considerations, The shape of the vessel can be a traditional cylinder, or can be more elliptical (as shown in FIG. 5) to more closely fit a user, and can range in sizes. Other possible configurations are shown in FIGS. 9 and 10.

The inner rubber coating or bladder 14 is preferably used to provide strength and to avoid corrosion. Rubber removes the problem of corrosion associated with aluminum liners used currently in the art, and removes the need to tumble vessels in order to remove any corrosion. Lack of corrosion should also ensure that the strength of the vessel will not diminish from its original design values.

Figure 7:
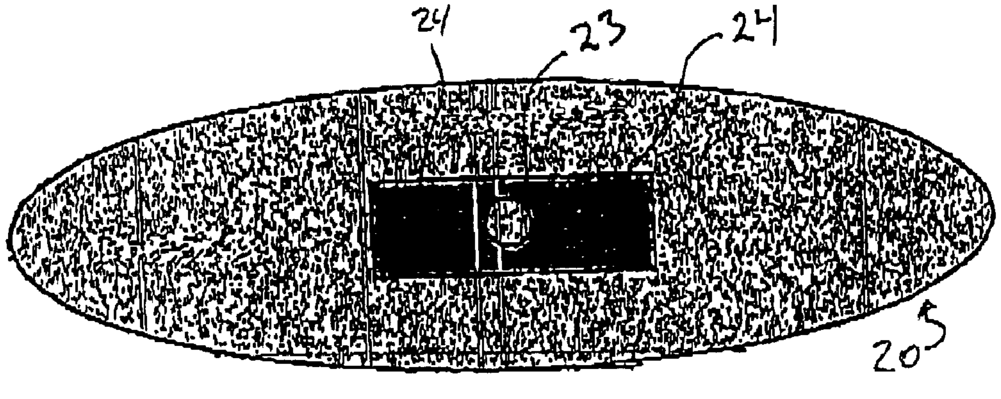
FIG. 7 is an end view of a wax module for creating the vessel of FIG. 3.
Figure 8:
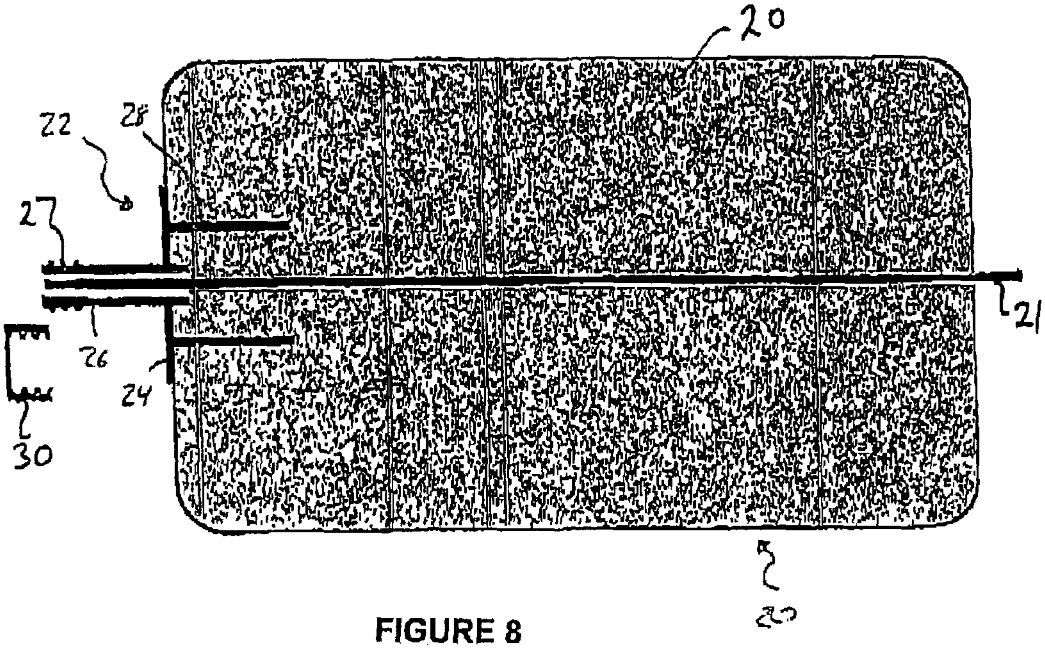
FIG. 8 is a side view of a wax module for creating the vessel of FIG. 3.

The inner rubber bladder 14 is created through the use of a wax module 20, as can be seen in FIGS. 7 and 8. Wax module 20 includes inlet fittings 22, as described below, and is dipped in liquid rubber and allowed to cure. An inner nylon liner can optionally be formed by rotomoulding. Alternatively, an aluminium anodized liner can be used instead of a rubber liner.

Once cured, the wax module 20 and inner bladder 14 are mounted on a lathe and the carbon filament is wound onto bladder 14. The filament would vessel and wax module are then heated in an oven at between 200 and 450 degrees Fahrenheit, depending on the epoxy used to bond the carbon filaments. The heating melts the wax module 20. The wax is drained away, leaving behind the bladder lining the interior of core 12.

The core 12 and bladder 14 are then preferably x-rayed for imperfections and quality assurance. Once this is done, the outer rubber layer 16 is created by dipping the assembly into liquid rubber. This outer rubber layer 16 provides strength and prevents hazardous materials from contacting the carbon fibre core. This protects against chemicals compromising the integrity of vessel 10.

Figure 16:
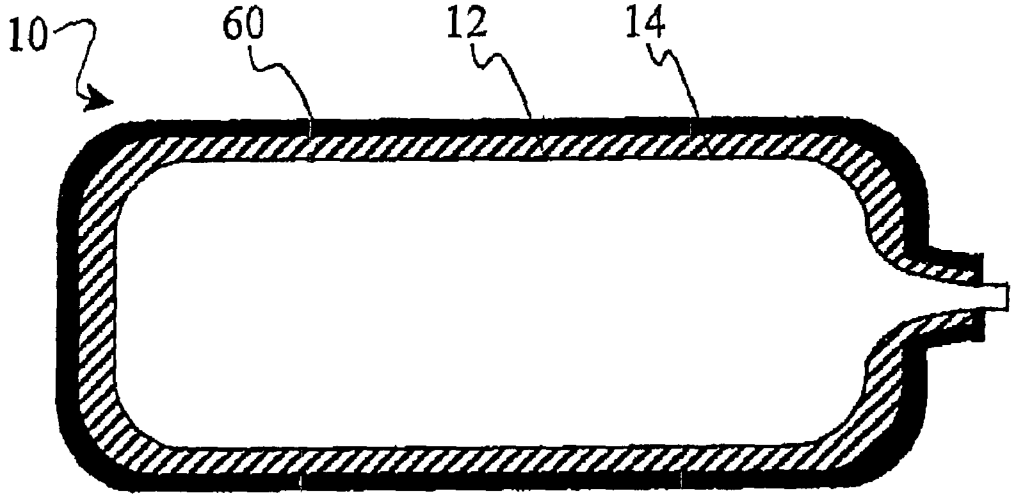
FIG. 16 is a cross sectional view of a vessel with a protective overwrap.
Figure 1:
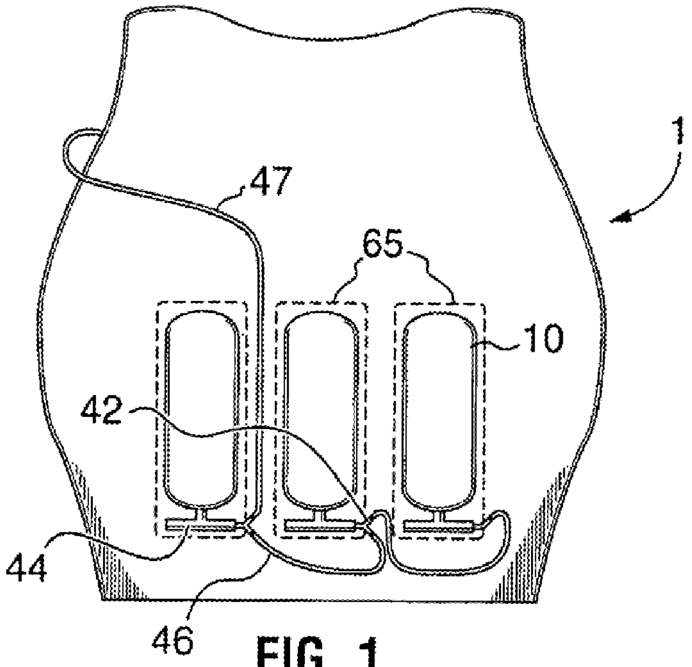
Figure 2:
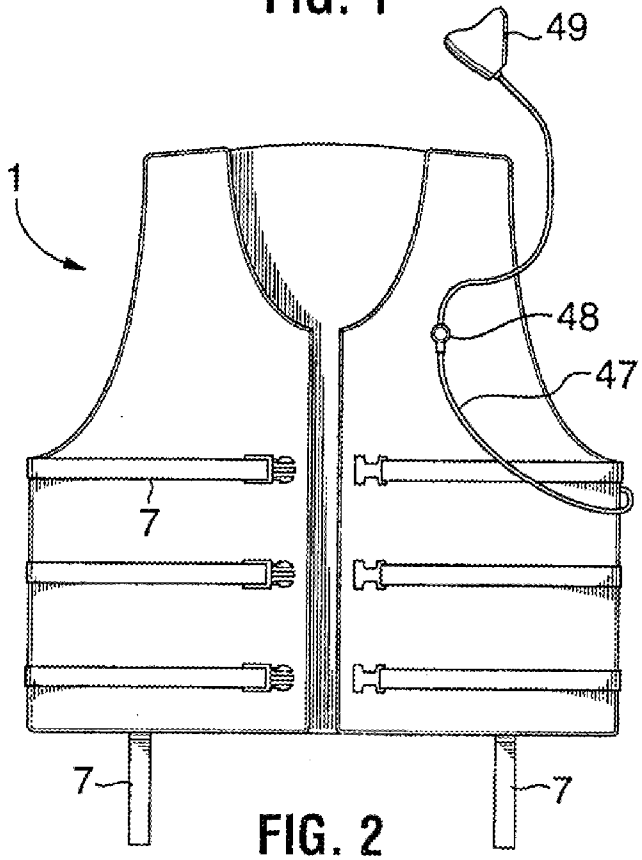
Figure 3:
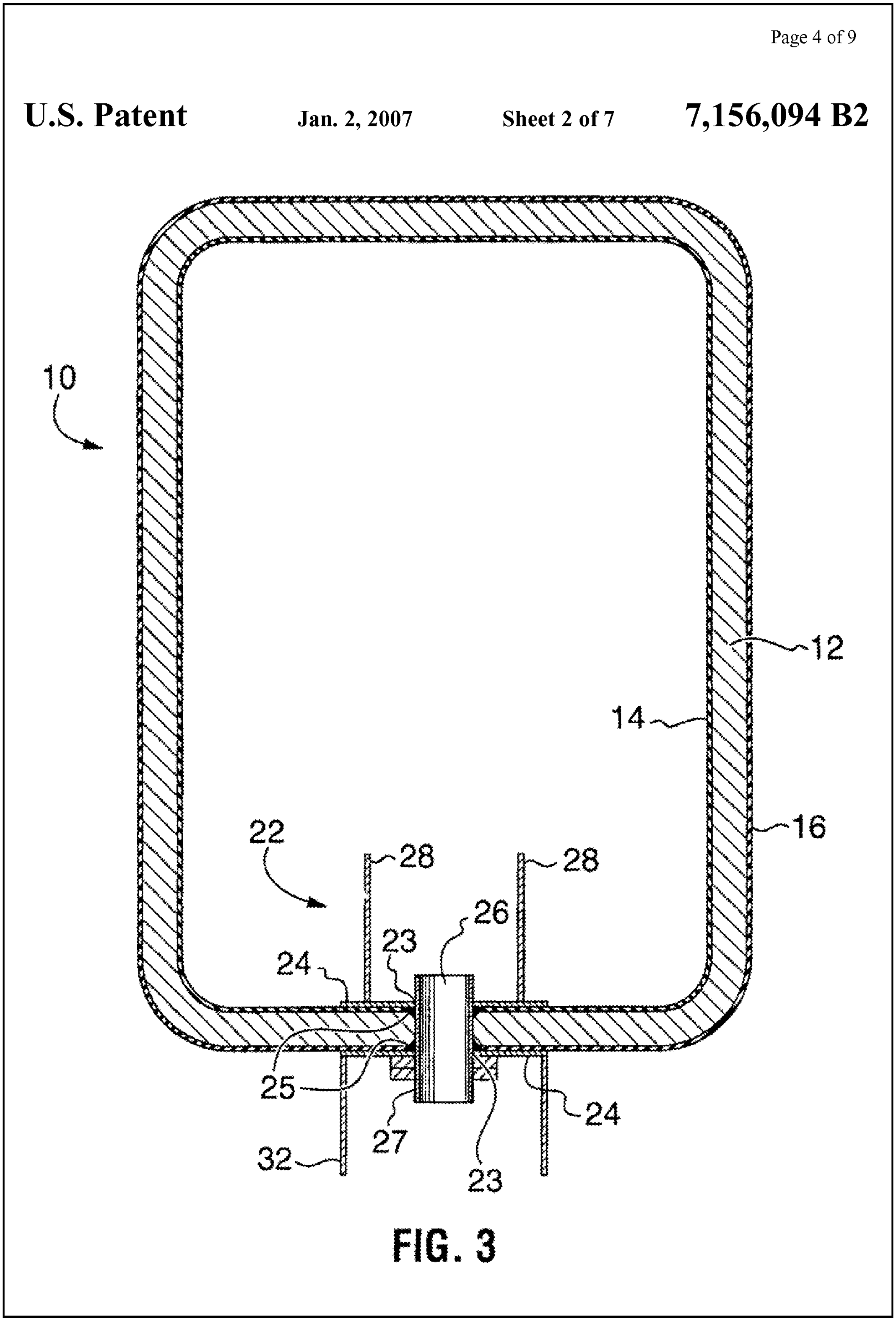
Figure 4:
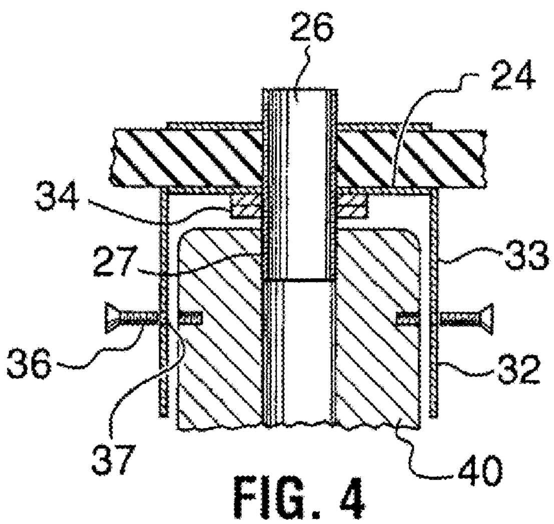
Figure 5:
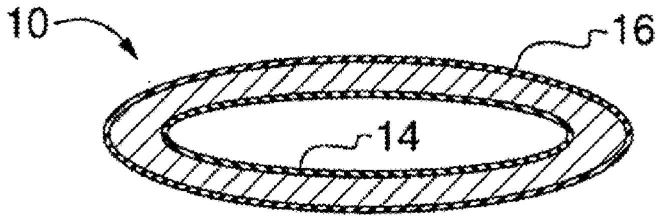
Figure 6:
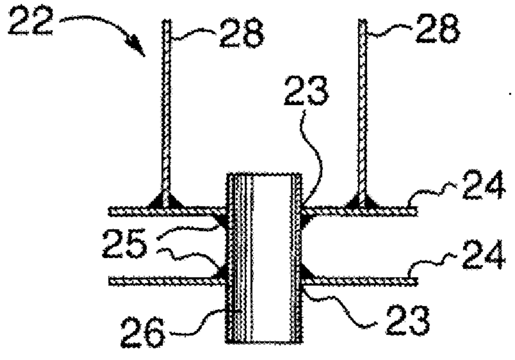
Figure 7:
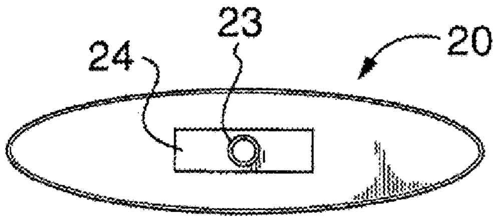
Figure 8:
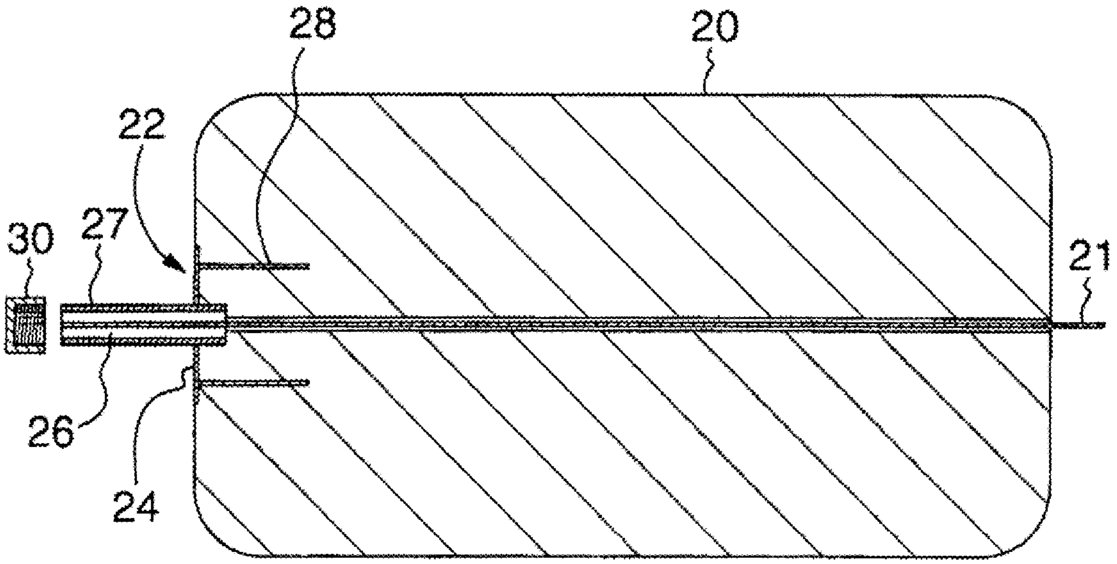
Figure 9:
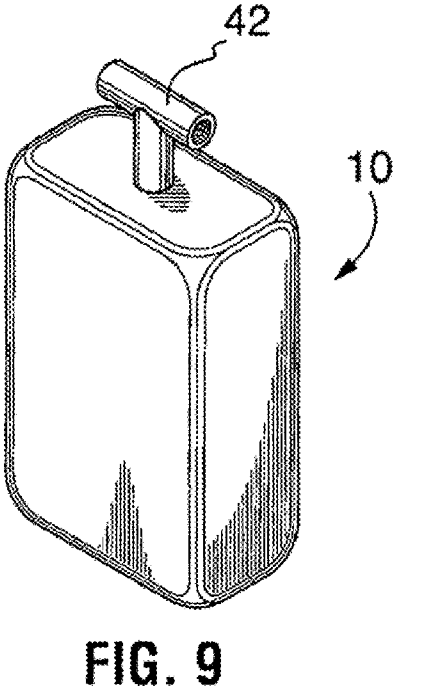
Figure 10:
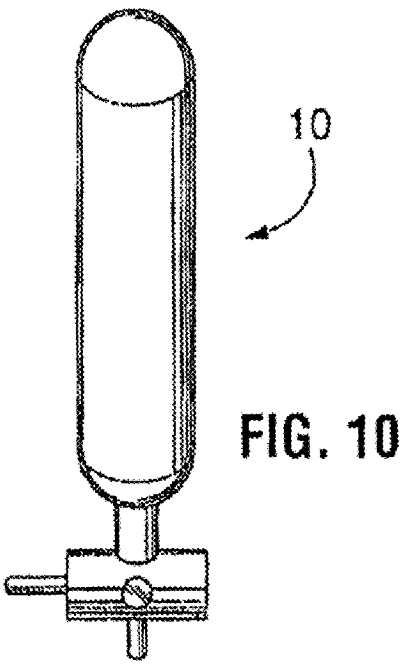
Figure 11:
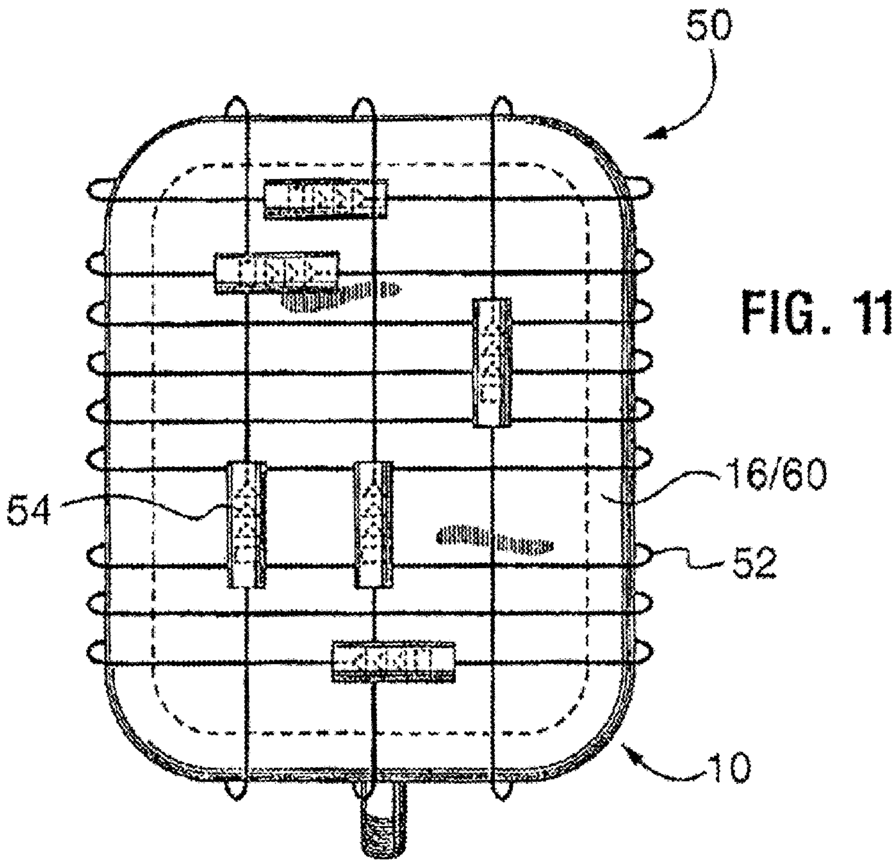
Figure 12:
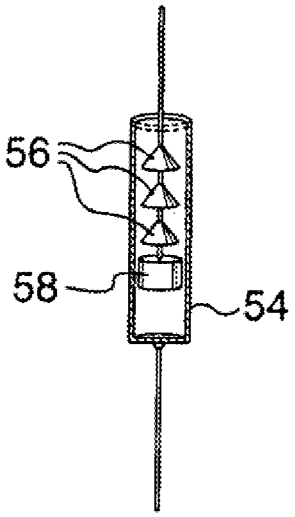
Figure 13:
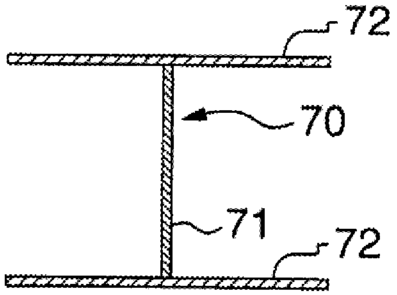
FIG. 13 PRIOR ART

In addition to, or instead of, outer rubber layer 16, a composite overwrap can be used. The overwrap is best seen in FIG. 16. This figure shows pressure vessel 10 comprised of liner 14 and core 12. Liner 14 can be a metal or rubber liner, as described above. Core, 12 can be a carbon fibre/epoxy mixture, as disclosed above. Core 12 allows vessel 10 to be filled to its preset pressure without rupturing.

Liner 14 may not be necessary if core 12 is comprised of stainless steel or aluminium. These materials provide enough containment to be used without a liner.

Over-wrap layer 60 is wound over core 12. Over-wrap layer 60 is comprised of a carbon composite thread that is immersed in a liquid rubber. Preferably the carbon composite thread consists of Kevlar™.

The thread and rubber are then filament wound around the vessel to a predetermined thickness. This winding may be done using a computerized lathe in order to achieve a uniform thickness about pressure vessel 10.

Once the winding is complete, pressure vessel 10 with its over-wrap layer 60 are then cured to solidify over-wrap layer 60.

The composite overwrap 60 of FIG. 16 could also be used on prior art pressure vessels to strengthen and protect these vessels.

Over-wrap 60 helps mitigate some of the disadvantages that pressure vessels currently have. In particular, due to the high strength of Kevlar™, present over-wrap layer 60 should provide complete containment in the case of a failure of the pressure vessel. This should therefore protect those around the pressure vessel who might previously have been harmed by high velocity fragments created by the failure of the pressure vessel. With the overwrap, pressure vessel 10 may be able to be pressurized closer to its maximum capacity, allowing more gas to be stored within the pressure vessel.

Also, the rubber within the windings creates better impact resistance for pressure vessel 10, further protecting it. Rubber will generally cushion an impact to the pressure vessel.

Still further, due to the rubber in the winding, the pressure vessel will be better able to withstand caustic environments, creating greater safety for those dependent on the pressure vessel.

Figure 3:
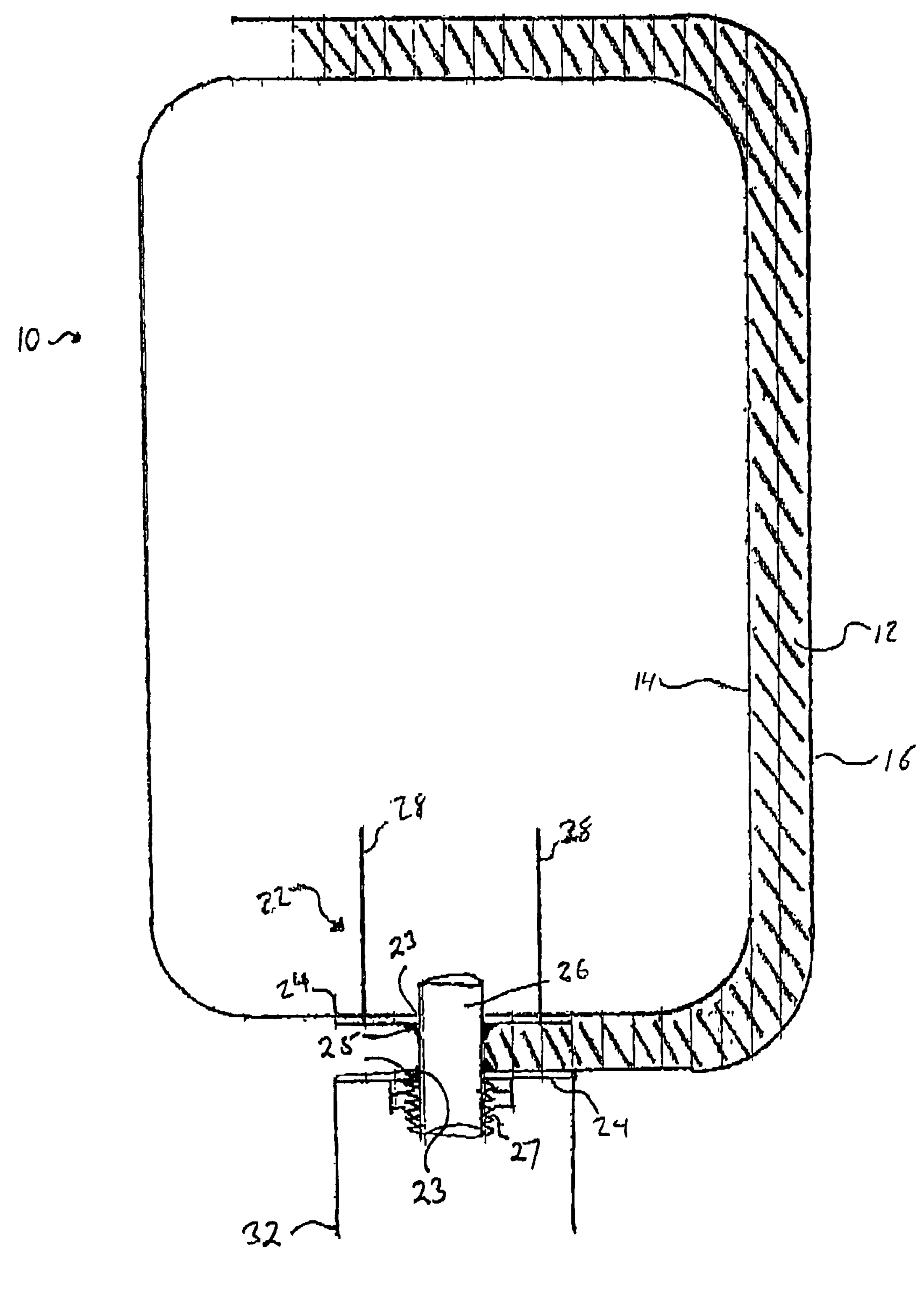
FIG. 3 is a cross sectional view of a preferred embodiment of a high pressure vessel and fitting.
Figure 4:
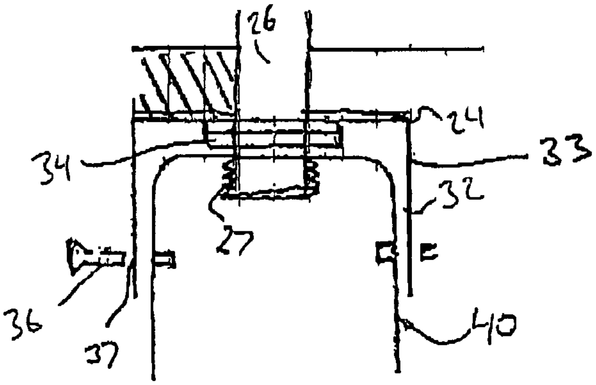
FIG. 4 is a cross sectional view of a second plate and nut arrangement that may be attached to the fittings of FIG. 2.
Figure 6:
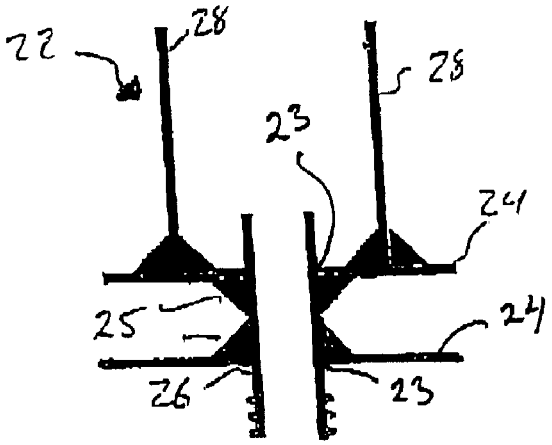
FIG. 6 is an enlarged cross sectional view of a portion of the vessel of FIG. 3.

The open end of each vessel 10 includes an inlet fitting 22, as can be seen in FIG. 3 and in greater detail in FIGS. 4 and 6. Inlet portion 22 includes two spaced apart stainless steel plates 24, each with a circular hole 23 in the centre. A cylindrical stainless steel air fitting 26 whose outer diameter fits concentrically within holes 23 in the steel plates is positioned through holes and the steel plates and air fitting

26 are then welded together at weldments 25. Steel plates 24 are arranged parallel to each other with the gap between them corresponding to the width of carbon fibre core 12 of vessel 10. When the carbon fibre is formed within this gap, its strength will ensure that fitting 22 will not be blown out of vessel 10 due to the pressures involved. This is further tested after the manufacture of the vessel by charging the vessel to considerably higher than the rated working pressure and ensuring that vessel 10 does not rupture and air fitting 22 remains in place, The steel plate 24 disposed towards the inner surface of vessel 10 further includes two flanges 28 welded to it or formed integrally therewith and protruding substantially perpendicularly to steel plate 24 and into vessel 10 and into wax module 20. This reduces the likelihood of wax module 20 moving during the filament winding process about spindle 21 as most clearly illustrated in FIG. 8 which shows the flanges anchored in the wax.

The outer end of the steel air fitting 26 is threaded at 27 to allow a cap 30 FIG. 8) to be added-to the fitting. Threads 27 can also be used to secure a second, plate 32 with a nut 34 or a nut/lock washer combination to outer steel plate 24 as shown most clearly in FIGS. 3 and 4.

Second plate 32 is shaped and adapted to accommodate regulator body housing 40 of a first stage regulator 44 (FIG. 1) as illustrated in FIG. 4. As can be seen from this figure, second plate 32 includes a skirt 33 with holes 37 for screws 36 that pass through the holes to connect regulator body 40 to second plate 32 for additional safety backing up the connection of regulator body 40 to threads 27 on fitting 26.

In operation, the vessels are charged and with reference to FIG. 1, air passes through first stage regulators 44 attached to the steel air fitting 26 of each vessel 10. A series of low pressure lines 46 connect all of the vessels together through the use of stainless "T" or "Y" fittings 42, and a low pressure supply line 47 is connected to a second stage regulator 48 on the front of the vest. Lines 46 and 47 are made from low pressure flexible pneumatic hose designed to withstand the pressures under which the vest is to be tested, or they may comprise metallic hose or a metallic manifold. Although pressure vessels 10 can be disposed on both the front and back of the vest, its contemplated that in most applications, the vessels will be confined to the vest's back, Second stage regulator 48 of the present vest apparatus is also selected of course to withstand the pressures under which the vessels are to be tested. In a preferred embodiment, the second stage regulator will be of a quick coupling mechanism type and will allow for the connection of multiple face masks or mouth pieces 49. i.e., one for a rescuer and one for the person being rescued. The regulator is placed on the vest in a location that allows easy and rapid connection of the face masks, The location should also allow a user to easily read a pressure gauge on the regulator. In a preferred embodiment the regulator will also have an alarm to signal to the user when the pressure falls below a certain level.

A respirator can be designed to easily attach to the second stage regulator. Various types of breathing apparatus are contemplated, including a mask to fit over a users nose and mouth, a simple mouth piece, a SCUBA respirator or a clear plastic anti-fogging hood, such as those currently used in the art.

Figure 11:
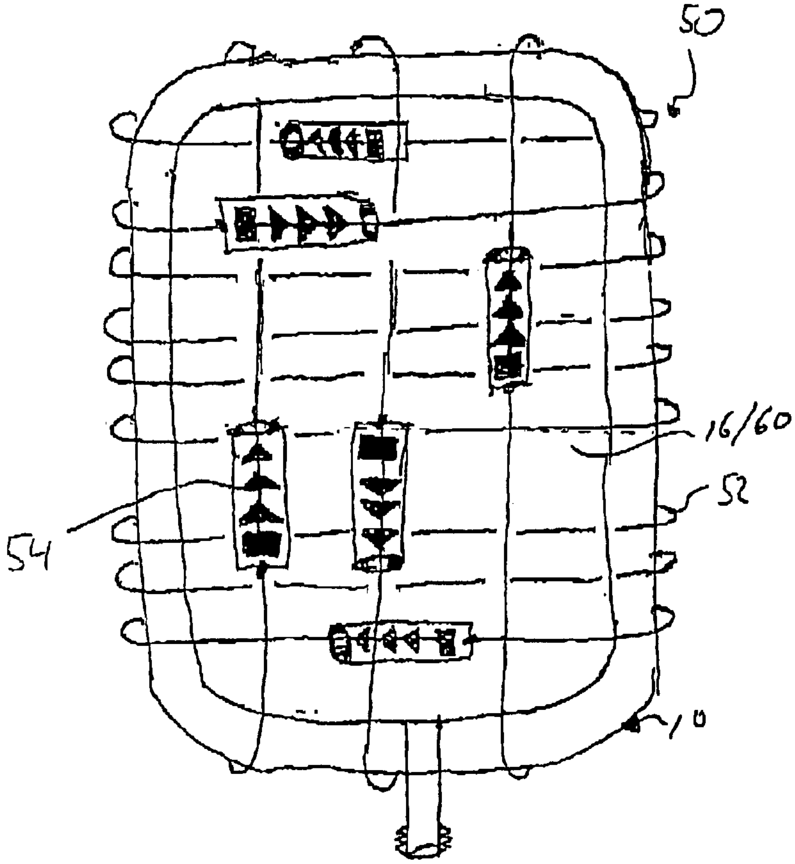
FIG. 11 is a schematical view of a containment bag for the vessel of FIG. 3.

Due to the high charge pressures of vessels 10, the vest apparatus further includes several safety features. The first is a containment bag 50 that is secured to the outside of vessel 10. A preferred containment bag 50 is shown in FIG. 11.

Containment bag 50 consists of braided stainless steel aircraft cable 52 woven around vessel 10 to resemble a fish net, preferably on approximately 2.5 cm squares. The dimensions of containment bag 50 allow virtually no clearance between the cable and the exterior rubber bladder 16 or overwrap 60 of vessel 10. This confines vessel 10, and in the case of an explosion or rupture, any propelled fragments are limited in size to the space between the braids. The rubber bladder 16 or overwrap 60 on the outer surface of vessel 10 should also act to further suppress any flying fragments.

Figure 12:
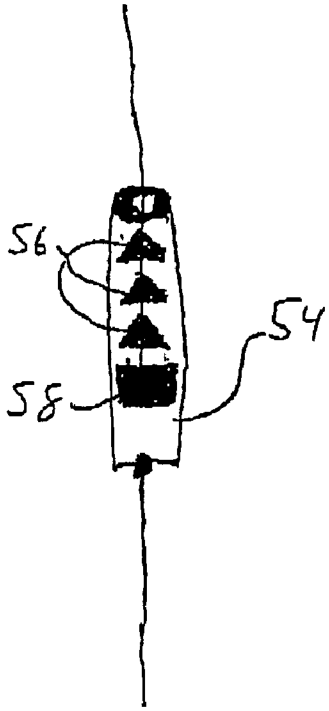
FIG. 12 is a cross sectional view of a suppression device used in the containment bag of FIG. 11.

Cable 52 of containment bag 50 is held in place through the use of special suppression lugs 54, a cross section of one of which is shown in FIG. 12. These suppression lugs 54 are crimped at strategic points on cable 52 to hold and tighten containment bag 50 in place. As can be seen in FIG. 12, each suppression lug 54 preferably includes three lead cones 56 and a stainless cable end anchor plug 58 to hold cable 52 within lug 54. The other end of cable 52 is permanently secured to lug 54, thus creating a closed loop. In the event of a repture of vessel 10, the compression of cones 56 between plug 58 and the end of lug 54 will dissipate energy.

The strength of cable 52, along with rubber bladder 16 or overwrap 60, should act to prevent any fragments from escaping from vessel 10. If, however, a fragment does escape, the present vest apparatus may further be provided with a novel deflection shield 65 disposed between the user and the vessel.

The defection shield is comprised of a material that should withstand and absorb the impact of a high speed fragment hitting it. In order to ensure that the weight and bulk of the vest apparatus is minimized, it is further desirable to ensure this deflection shield is as thin and light in weight as possible. This is accomplished through the use of a new composite material.

Figure 13:
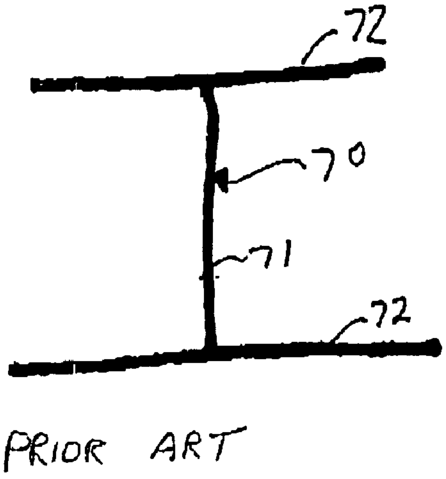
FIG. 13 is the prior art configuration of an "I-beam" balsa wood core composite.
Figure 14:
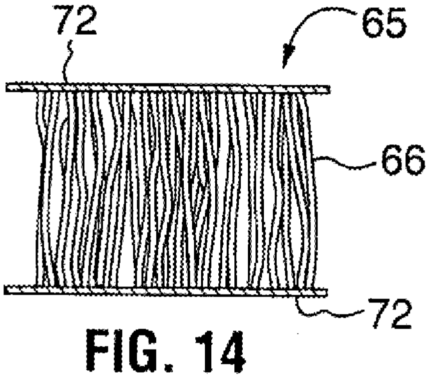
FIG. 14 is a cross section showing a new pure carbon fibre composite material.
Figure 15:
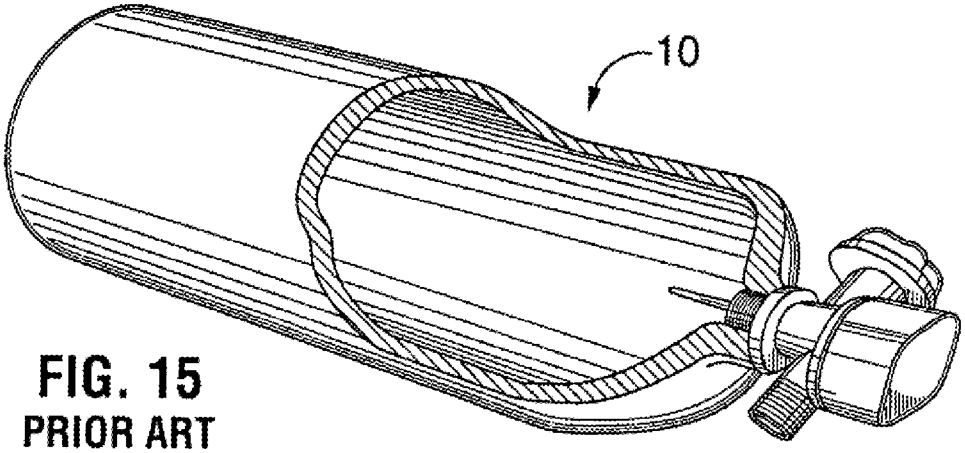
FIG. 15 PRIOR ART
FIG. 15 is a view of a prior art regulator-valve body assembly.
Figure 16:
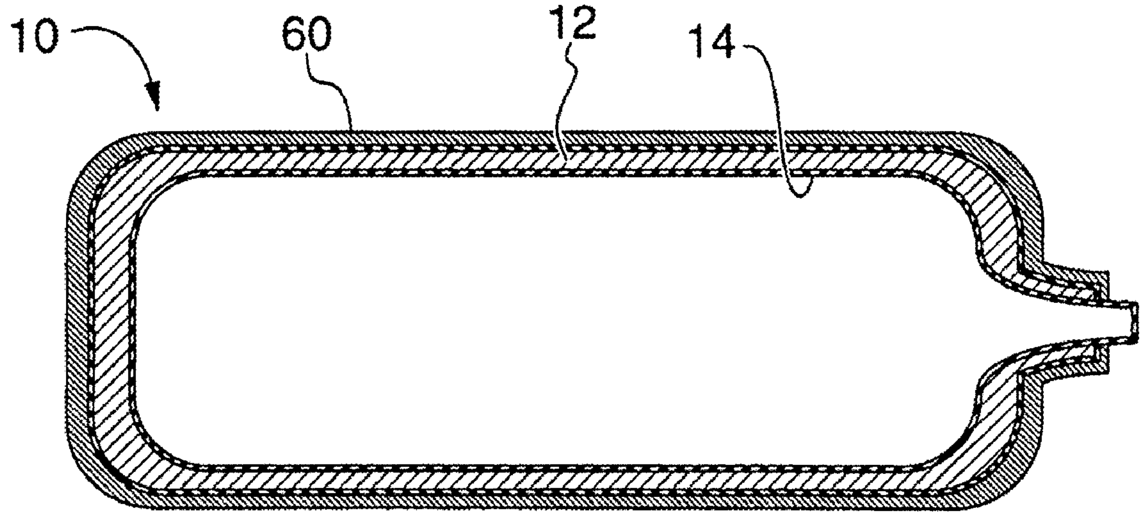

Prior art for carbon composite materials includes the "I-beam" configuration 70 as shown in FIG. 13. This type of core is referred to as "End-Grain-Balsa", wherein the vertical portion 71 of the I-beam is balsa wood, and the horizontal portions 72 above and below the "I" are applied carbon fibre fabric, The present deflection shield 65 (shown in FIG. 14) comprises carbon fibre and high quality epoxy, providing higher impact resistance than most core materials, For this improvement, the balsa wood core of previous composites is replaced with vertical carbon fibre strands 66. This core preferably measures between one-eighth of an inch to more than two inches in thickness depending upon the level of protection required. The carbon fibres are continuous-roving, pre-impregnated tow, meaning the fibres have been previously impregnated in an epoxy-bath with epoxy which will begin its cure process with the introduction of heat and light.

The core of the present composite is preferably created by placing fibres in a trough approximately 6-inches wide by 6 inches deep by three feet in length. The trough has a plastic liner allowing the fibres to easily move in the trough. The finished material can be cut to a predetermined thickness using known techniques.

The out slices are placed on a sheet of pre-impregnated carbon fibre fabric 72. A second layer of the fabric 72 is placed on top of the slice, creating a pure carbon fibre core material. The material is then placed in refrigerated storage until ready for delivery. The present invention further contemplates using this new core for other uses besides deflection plates.

All of the above components are placed within a vest as may be seen in FIG. 1. The vest is constructed in a compartmentalized fashion such that the components are of sufficient capacity to allow for the easy insertion and removal of the vessels. The number of vessels is dependant upon the size of the vessels and the physical size of a user's vest, where a child's vest may only accommodate four vessels for example, and an extra large vest may include twelve vessels. Each compartment further allows a deflector plate 65 to be installed behind the vessel, protecting the user in case the vessel explodes or ruptures.

The compartments of the vest are evenly distributed on the back of the vest but they can also be distributed on the front and the back if desired.

In one embodiment of the present invention, the vest is constructed to incorporate a "quick connect" strap 7 under the buttocks of a user to prevent the vest from rising and interfering with the face mask. The vest may also include a drawstring at its bottom which can be used to tighten the bottom of the vest.

FIG. 1 shows vest 1 which includes a series of vessels 10 located at various points along a user's back. Vessels 10 are interconnected with a series of first stage regulators 44 and hoses 46 which connect to second stage-regulator 48 on the vest's front.

As described above, second stage regulator 48 is placed in a location that is easily accessible to a user to allow for both the connection of a respirator and to facilitate the checking of the amount of air left in the vessels. This location would generally be at chest height and on the front of the garment.

The vest can further include storage compartments into which the respirator fits, such that the respirator can easily be accessed in the case of an emergency, Other embodiments envisioned include a storage compartment for a spare mask or hood allowing the rescue of a victim during an emergency.

The material the vest is made from will depend on its intended application. If the vest is to be used in a fire rescue situation, the material can be the same as that presently used in fire fighting clothing, and thus be fire resistant. Conversely, if the vest is to be used in mountaineering or marine environments, it can be constructed of a insulating or waterproof fabric.

The air vest device thus provides a compact system with a considerably longer air supply than current self contained breathing apparatus on the market, it is envisioned that the vest may be used for a number of applications including: fire fighting, oil field and gas plant operations, mining operations, underwater diving environments, search and rescue units, industrial chemical processing plants, NASA, passenger aircraft personnel, police tactical units, and armed forces world-wide.

The above-described embodiments of the present invention are meant to be illustrative of preferred embodiments of the present invention and are not intended to limit the scope of the present invention. Various modifications, which would be readily apparent to one skilled in the art, are intended to be within the scope of the present invention. The only limitations to the scope of the present invention are set out in the following appended claims.

The invention claimed is:

1. A wearable garment apparatus capable of supplying air to a user comprising:
- a plurality of compartments disposed about said garment;
- a plurality of air storage means for fitting into respective ones of said compartments;
- regulator means;
- conduit means for connecting said plurality of air storage means to said regulator means;
- a breathing member connected in fluid communication to said regulator means; and
- containment means disposed about each of said air storage means, said containment means comprising:
  - a plurality of wires wrapped laterally and longitudinally in a grid pattern about each said air storage means, and
  - a plurality of fastening means for securing ends of respective wires, said fastening means being energy absorbing for controlled expansion of the wire connected thereto in the event of failure of said air storage means;
- wherein said breathing means allows a user to receive air from said plurality of air storage means.

2. The apparatus of claim 1 further comprising a shield member disposed within said compartments between said air storage means therein and said user, whereby said shield member protects said user against failure of said air storage means.

3. The apparatus of claim 1 wherein said air storage means comprise:
- an inner bladder;
- a structural core;
- an outer cover; and
- an air outlet;
- wherein said inner bladder fits concentrically within said core and said core fits concentrically within said outer cover, and whereby said air outlet provides fluid communication for air egressing said storage means during discharge and ingressing said storage means during recharge.

4. The apparatus of claim 3 wherein said structural core is comprised of carbon fibre.

5. The apparatus of claim 4 wherein said inner bladder is made of rubber.

6. The apparatus of claim 5 wherein said shield member is comprised of a composite carbon fibre material.

7. The apparatus of claim 6 wherein air pressure within said air storage means is charged to between 3000 and 7500 psi.

8. The apparatus of claim 1 wherein said breathing means is an anti-fog hood, a face mask, a mouth piece, a respirator or a SCUBA respirator.

* * * * *

UNITED STATES PATENT AND TRADEMARK OFFICE

CERTIFICATE OF CORRECTION

PATENT NO. : 7,156,094 B2
APPLICATION NO. : 10/117325
DATED : January 2, 2007
INVENTOR(S) : Nicholas Anthony Chornyj It is certified that error appears in the above-identified patent and that said Letters Patent is hereby corrected as shown below:

Delete the title page showing an illustrative figure and substitute the attached title page therefor.

Delete drawing sheets 1-10 and substitute the attached drawing sheets containing figures 1-16 therefor.

Signed and Sealed this

Fourteenth Day of July, 2009

JOHN DOLL

*Acting Director of the United States Patent and Trademark Office*

(12) United States Patent
Chornyj

(10) Patent No.: US 7,156,094 B2
(45) Date of Patent: Jan. 2, 2007

(54) BREATHING APPARATUS AND PRESSURE VESSELS THEREFOR

(75) Inventor: Nicholas Anthony Chornyj, Fort McMurray (CA)

(73) Assignee: Failsafe Air Vest Corporation, Reno, NV (US)

(*) Notice: Subject to any disclaimer, the term of this patent is extended or adjusted under 35 U.S.C. 154(b) by 747 days.

(21) Appl. No.: 10/117,325

(22) Filed: Apr. 8, 2002

(65) Prior Publication Data

US 2002/0153009 A1 Oct. 24, 2002

(30) Foreign Application Priority Data

Apr. 6, 2001 (CA) .................................... 2353454
Jul. 19, 2001 (CA) .................................... 2353298

(51) Int. Cl.
*A61M 15/00* (2006.01)

(52) U.S. Cl. .......................... 128/202.19; 128/204.26; 128/205.22

(58) Field of Classification Search .......... 128/201.29, 128/202.19, 204.26, 205.22; 220/585, 586, 220/588, 589, 592, 645, 646, 647, 648
See application file for complete search history.

(56) References Cited

U.S. PATENT DOCUMENTS 1,288,857 A * 12/1918 Farr .................... 128/205.22
1,419,395 A * 6/1922 Mackenzie .................. 52/511
1,608,264 A * 11/1926 Germano .............. 128/201.22
1,630,209 A * 5/1927 Olgard ................ 128/206.26
1,982,852 A * 12/1934 Bergstrom et al. ........... 285/55
2,109,529 A * 3/1938 Goddard ................ 244/117 R
2,335,038 A * 11/1943 Bridges ...................... 220/646
2,339,554 A * 1/1944 Kuhn ........................ 220/592
2,376,831 A * 5/1945 Stearns ..................... 220/586
2,380,372 A * 7/1945 Alderfer .................... 244/148
2,381,396 A * 8/1945 Kuhn ........................ 220/592
2,507,778 A * 5/1950 Frey ........................ 220/585
2,844,145 A * 7/1958 Berge .................. 128/205.22
2,844,939 A * 7/1958 Schultz ...................... 60/257
3,074,584 A * 1/1963 Curzon ...................... 220/591
3,228,549 A * 1/1966 Courtney .................... 220/589
3,490,638 A * 1/1970 Francois et al. ........... 220/565
3,540,615 A * 11/1970 Burkley et al. ........ 220/560.13
4,118,262 A * 10/1978 Abbott ...................... 156/175
4,932,403 A * 6/1990 Scholley ............... 128/205.22
4,964,405 A * 10/1990 Arnoth ................ 128/205.17
5,036,845 A * 8/1991 Scholley ............... 128/205.22
5,127,399 A * 7/1992 Scholley ............... 128/205.22
5,188,267 A 2/1993 Sargent et al.
5,287,987 A 2/1994 Gaiser
5,309,571 A 5/1994 Huang
5,370,113 A * 12/1994 Parsons ............... 128/205.22
5,385,262 A * 1/1995 Coquet et al. ............ 220/589

(Continued)

FOREIGN PATENT DOCUMENTS

EP 506256 9/1992

(Continued)

*Primary Examiner*—Aaron J. Lewis
(74) *Attorney, Agent, or Firm*—Dennison, Schultz & MacDonald

(57) ABSTRACT

There is described a wearable garment capable of supplying air to a user comprising a plurality of compartments disposed about the garment, a plurality of air storage vessels for fitting into respective ones of the compartments, an air regulator, a connector for connecting the plurality of air storage vessels to the regulator, and a breathing member connected to the regulator in fluid communication therewith, wherein the breathing member allows a user to receive air from the plurality of air storage vessels.

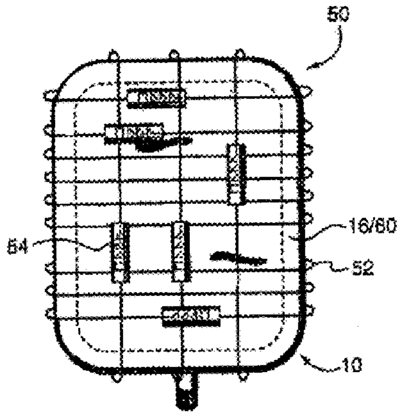

8 Claims, 7 Drawing Sheets